United States Patent
Ofori et al.

(12) 
(10) Patent No.: US 6,310,232 B1
(45) Date of Patent: Oct. 30, 2001

(54) METHOD FOR RECYCLE OF BROMIDE-CONTAINING CATALYST CONSTITUENTS

(75) Inventors: John Yaw Ofori, Niskayuna; Eric James Pressman, East Greenbush; Ben Purushotam Patel, Niskayuna, all of NY (US); Phillip Oscar Moreno, Eugene, OR (US); Richard Anthony Battista, Dalton, MA (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/709,805

(22) Filed: Nov. 10, 2000

(51) Int. Cl.[7] .................... C07C 69/96; C07C 277/00; C07C 279/00; C07F 9/02
(52) U.S. Cl. .................... 558/274; 558/260; 558/270; 564/230; 564/281; 568/10
(58) Field of Search .................... 558/260, 270, 558/274; 564/281, 230; 568/10

(56) References Cited

U.S. PATENT DOCUMENTS

| | | |
|---|---|---|
| 4,187,242 | 2/1980 | Chalk . |
| 5,231,210 | 7/1993 | Joyce et al. . |
| 5,239,106 | 8/1993 | Shafer . |
| 5,284,964 | 2/1994 | Pressman et al. . |
| 5,373,083 | 12/1994 | King et al. . |
| 5,380,907 | 1/1995 | Mizukami et al. . |
| 5,399,734 | 3/1995 | King et al. . |
| 5,498,789 | 3/1996 | Takagi et al. . |
| 5,502,232 | 3/1996 | Buysch et al. . |
| 5,543,547 | 8/1996 | Iwane et al. . |
| 5,625,091 | 4/1997 | Buysch et al. . |
| 5,726,340 | 3/1998 | Takagi et al. . |
| 5,760,272 | 6/1998 | Pressman et al. . |
| 5,821,377 | 10/1998 | Buysch et al. . |
| 5,856,554 | 1/1999 | Buysch et al. . |
| 5,981,788 | 11/1999 | Ofori et al. . |
| 6,114,564 | 9/2000 | Pressman et al. . |
| 6,172,254 | 1/2001 | Pressman et al. . |
| 6,180,812 | 1/2001 | Johnson et al. . |

FOREIGN PATENT DOCUMENTS

| | | |
|---|---|---|
| 071286 | 2/1983 | (EP) . |
| 736325 | 3/1996 | (EP) . |
| 1102566 | 2/1968 | (GB) . |
| 94-271506 | 9/1994 | (JP) . |
| 94-271509 | 9/1994 | (JP) . |
| 95-145107 | 6/1995 | (JP) . |
| 96-89810 | 4/1996 | (JP) . |
| 96-92168 | 4/1996 | (JP) . |
| 96-193056 | 7/1996 | (JP) . |
| 97-110804 | 4/1997 | (JP) . |
| 97-255629 | 9/1997 | (JP) . |
| 97-278715 | 10/1997 | (JP) . |
| 97-278716 | 10/1997 | (JP) . |
| 10-158221 | 6/1998 | (JP) . |
| 10-316627 | 12/1998 | (JP) . |

OTHER PUBLICATIONS

Application Ser. No. 09/383,424, filed Aug. 27, 1999; "Catalyst Composition and Method for Producing Diaryl Carbonates", Bruce Fletcher Johnson et al.

*Primary Examiner*—Sreeni Padmanabhan
*Assistant Examiner*—Sikarl A. Witherspoon
(74) *Attorney, Agent, or Firm*—Noreen C. Johnson; S. Bruce Brown

(57) ABSTRACT

Bromide source such as alkali metal bromide, alkaline earth metal bromide, or onium bromide, present as part of a catalyst mixture in an organic oxidative carbonylation mixture further comprising diaryl carbonate and a hydroxyaromatic compound, is often at least partially converted to organic bromide such as bromophenols. The bromide source can be recycled after reaction through treatment with an aqueous acidic bromide solution such as hydrogen bromide, preferably after removal of a major proportion of hydroxyaromatic compound such as phenol.

21 Claims, No Drawings

METHOD FOR RECYCLE OF BROMIDE-CONTAINING CATALYST CONSTITUENTS

BACKGROUND OF THE INVENTION

This invention relates to catalyst recycle, and more particularly to the conversion and recycle of bromide-containing constituents of catalyst compositions used to conduct chemical reactions.

The use as catalysts of various compositions comprising transition metals is known. Among the catalyst constituents in common use are compounds of the Groups 8, 9, and 10 metals, including those having atomic numbers of at least 44 (i.e., ruthenium, rhodium, palladium, osmium, iridium and platinum), hereinafter "heavy transition metals". Compounds of other metals, such as those of Group 8, 9, and 10 with atomic numbers less than 44, and including cobalt, lead, manganese, cerium, titanium, and copper are also useful as constituents of said catalyst compositions.

Bromide sources are also frequently present in various catalyst compositions. These include alkali metal and alkaline earth metal bromides, and onium salts, including trialkylamine hydrobromides and tetraalkylammonium, tetraalkylphosphonium, hexaalkylguanidinium, and sulphonium bromides.

The reactions in which such compounds serve a catalytic function include some which involve organic compounds as reactants, products or both. An illustration is the catalytic carbonylation of hydroxyaromatic compounds such as phenol with carbon monoxide and oxygen to yield diaryl carbonates such as diphenyl carbonate. This reaction will sometimes be designated "carbonylation" hereinafter.

In a typical carbonylation reaction, phenol is combined with a compound of a heavy transition metal, most often palladium, and other catalytic species which may include organic and inorganic co-catalysts and at least one bromide source. One or more other metal compounds, most often of lead, may be used as inorganic cocatalysts, and the use in combination therewith of bromide sources which may include alkali metal or alkaline earth metal bromides, tetraalkylammonium bromides, or hexaalkylguanidinium bromides is frequently advantageous. The resulting mixture is pressurized with carbon monoxide and oxygen to yield a product mixture containing diphenyl carbonate, unreacted phenol and by-products which include palladium in elemental and/or combined form and compounds of other metals present in the catalyst composition.

In U.S. Pat. No. 5,981,788, there is described a method of recovering and recycling carbonylation catalyst constituents which include heavy transition metals such as palladium, other metals including those of the Groups 8, 9, and 10 with atomic numbers less than 44 such as cobalt, and bromide sources such as tetraalkylammonium and hexaalkylguanidinium bromides. The recovery of the bromide source comprises simply its extraction with water, optionally following a preconcentration to lower the phenol concentration. This is practical when the other metal is cobalt, since there is essentially no chemical interaction in the presence of cobalt between hydroxyaromatic compounds such as phenol and bromide ions.

However, many of the numerous other metals employed in such catalyst compositions are not as suitable as cobalt in maintaining the presence of ionic bromide. This is particularly true of lead, which, when present, promotes conversion of the ionic bromide, typically an amount in the range of about 30–95% by weight thereof, to covalently bound bromine in the form of organic bromine compounds, predominantly bromophenols such as 2- and 4-bromophenol. Other metals can produce the similar covalently bound bromine compounds.

Conversion of ionic bromide to covalent bromine makes recovery of the cationic portion of the bromide source difficult. This may be the result of association of the cation with organic anions such as phenate. In addition to this difficulty of recovery, most ionic molecules in which the anion is a non-halogen such as phenate are not appreciably active as catalyst constituents.

It is of interest, therefore, to provide a method for recovery of bromide sources and their conversion or reconversion to compounds capable of supplying bromide ion to a catalyst composition.

SUMMARY OF THE INVENTION

The present invention is based on the discovery that a simple bromide contact step under proper conditions can reconvert the cationic portion of the bromide source to an active bromide-containing catalyst material.

In one embodiment the invention is a method for removal and recycle of ionic bromide-containing catalytic materials from a composition comprising a substantially water-insoluble organic material and comprising a bromide source, which method comprises the steps of contacting said composition with an aqueous acidic solution comprising bromide ions, thereby regenerating said bromide source, and extracting said bromide source with an aqueous liquid.

DETAILED DESCRIPTION; PREFERRED EMBODIMENTS

The method of the invention is particularly applicable to carbonylation reaction mixtures comprising at least one diaryl carbonate such as diphenyl carbonate, which is essentially water-immiscible. Unreacted hydroxyaromatic compound, such as phenol, may also be present. It is considerably more soluble in water than is diaryl carbonate. It should be understood, however, that the method of the invention may be applied equally well to any reaction affording as product an organic material having low solubility in water and employing a catalyst comprising any heavy transition metal compounds and other catalytically active metal compounds.

Also present in carbonylation reaction mixtures are catalyst constituents including a heavy transition metal compound, particularly at least one based on palladium. Typical palladium compounds which are employed as carbonylation catalysts are the salts of divalent palladium with carboxylic acids such as acetic acid and $\beta$-diketones such as 2,4-pentanedione (acetylacetone).

Co-catalysts, usually inorganic and sometimes in combination with organic, are also generally present, the inorganic co-catalyst being at least one metal compound and especially, for the purposes of this invention, a compound of a metal other than cobalt. Most often, the metal is at least one metal selected from the group consisting of lead, manganese, cerium, titanium, and copper, and mixtures thereof.

Bromide sources which may be present in the catalyst composition include alkali metal bromides, alkaline earth metal bromides, and onium salts, including trialkylamine hydrobromides and tetraalkylammonium, tetraalkylphosphonium, hexaalkylguanidinium, and sulphonium bromides; illustrative are sodium bromide, tetramethylammonium bromide, tetra-n-butylammonium bromide and hexaethylguanidinium bromide. Suitable organic cocatalysts include various terpyridine, phenanthroline, quinoline and isoquinoline compounds, with 2,2'.6',2"-terpyridine often being preferred. These compounds and the by-products formed therefrom are generally incorporated in the organic phase during carbonylation.

The major product of the carbonylation reaction is usually a substantially homogeneous organic liquid containing diaryl carbonate (typically diphenyl carbonate), excess hydroxyaromatic compound (typically phenol) and palladium compounds, inorganic co-catalytic compounds or their by-products and bromide sources or their by-products. Also present may be organic co-catalysts such as terpyridines, or their by-products. This organic liquid may also contain covalent bromine compounds, typically bromophenols, formed by the reaction of bromide with the hydroxyaromatic compound in the presence of the other catalyst constituents.

Prior to performing the method of the invention, it is generally preferred to remove about 30–99%, preferably a major proportion, generally about 75–90% by weight, of the hydroxyaromatic compound from the organic liquid. Removal may be achieved by methods known in the art, such as simple vacuum stripping.

In an embodiment of the present invention, the organic liquid is contacted with an aqueous acidic solution containing bromide ions. Said solution is preferably of hydrogen bromide, but other acidic bromides may also be employed. A typical solution for this purpose will comprise about 0.5–50%, preferably about 0.5–6% and most preferably about 1–4% by weight hydrogen bromide, with the balance being water.

The amount of acidic bromide solution employed should be an amount effective to convert all of the cationic portion of the bromide source material to bromide. The amount necessary can be calculated from the amount of bromide source in the catalyst composition before reaction and the proportion of organic bromine compounds in the organic liquid, the latter being determinable, for example, by a standard high performance liquid chromatographic analysis which may be routinely performed in addition to analyzing for hydroxyaromatic compound and diaryl carbonate. Any bromide that has not been converted to organic bromine compounds is still present as ionic bromide.

Thus, the amount of acidic bromide solution is at least equivalent to the bromide converted to organic bromine compounds. However, it is also within the scope of the invention to employ an excess of acidic bromide, most often at least a 10% molar excess with respect to bromide source originally present. The amount of bromide employed in excess is not critical, but there is seldom any advantage in using more than a 50% molar excess. Alternatively, the amount of acidic bromide solution employed may be stoichiometrically equivalent to or in excess of the total amount of bromide originally present in the organic mixture.

Treatment of the organic mixture with acidic bromide solution typically includes agitation so as to provide intimate mixing and should be for a time effective to convert the cation originally present in the bromide source to the corresponding bromide. An adequate time for this purpose is generally in the range of about 1–30 minutes and preferably about 3–10 minutes, and can be easily determined by simple experimentation. Following said treatment, the organic and aqueous phases are separated. For ease of separation, it is preferred that the difference in density between the aqueous and organic phases be at least about 0.05 grams per milliliter (g/ml) and preferably at least about 0.08 g/ml, and the concentration of the aqueous and organic phases can also be easily adjusted in that respect.

The reconstituted bromide source may pass by extraction into the aqueous acidic bromide solution, from which it can be recovered and recycled. It is also effective, however, to first reconstitute the bromide source, for example using anhydrous hydrobromic acid, and subsequently to remove it from the organic liquid by extraction. Such extraction may typically be with water, most often with several portions of water. It is possible to then remove the water by evaporation or an equivalent operation, recovering bromide source and recycling it for further use.

The invention is illustrated by the following examples. All parts and percentages are by weight.

EXAMPLE 1

A 1219.4-part post-carbonylation reaction mixture comprising diphenyl carbonate and unreacted phenol and, prior to performance of the carbonylation reaction, containing 25 ppm of palladium as palladium(II) 2,4-pentanedionate, 56 equivalents (per equivalent of Pd) of lead as lead(II) oxide and 30.97 parts (201.1 millimoles [mmol]) of tetramethylammonium bromide (TMAB) was evaporated under vacuum (100° C./2 torr) to remove volatile species, primarily phenol, until there remained 267 parts of material. Of this amount, 132.1 parts, estimated to contain the equivalent of 15.32 parts (99.5 mmol) of TMAB (as TMAB, TMA phenate, and/or other TMA salts), was used in a further experiment to recover bromide source present in the distillation bottoms.

This sample was treated with a mixture of 14.6 parts of about 48% hydrogen bromide solution (about 86 mmol HBr) and 14.5. parts of water, the proportion of bromide being calculated to provide an amount of bromide ion equivalent to the organic bromide in the sample. (Typically, 30–80% of the bromide is converted to organic bromide.) The mixture was stirred for 10 minutes at 80° C. and the aqueous and organic phases were separated. The organic phase obtained was extracted five times with water (115.3, 124.7, 142.7, 129.5, 133.9 parts, respectively).

The combined aqueous extracts were extracted three times with methylene chloride (59.1, 60.0 and 64.8 parts, respectively) to remove phenol and other organic materials. The aqueous phase was then vacuum stripped at 80° C./10 torr to give 12.1261 parts of solid. Assuming that the 132.1 parts of the residue remaining after evaporation that was used contained the equivalent of 15.32 parts (i.e., 49.48% of the initial 30.97 parts) of TMAB present in the initial reaction mixture, the crude recovery was 79.1%.

EXAMPLE 2

The product of Example 1 was used, without any further treatment, in a carbonylation reaction. Using 60.4865 parts of phenol, 0.00049 part of Pd(II) 2,4-pentanedionate, 0.2063 part of lead(II) oxide and 1.5907 parts of crude TMAB, 19.1% diphenyl carbonate was produced in 1.5 hours. A similar run with 61.3922 parts of phenol. 0.00054 part of palladium(II) 2,4-pentanedionate, 205.6 9 lead(II) oxide and 1.5903 parts of fresh TMAB produced a similar level of D PC (16.9% in 1.5 hours).

EXAMPLES 3–9

A series of experiments was performed to determine the influence of various conditions on the extractability of TMAB from carbonylation reaction mixtures. The starting material was an organic product mixture containing diphenyl carbonate, phenol, palladium(II) 2,4-pentanedionate, lead(II) oxide and TMAB, enriched with diphenyl carbonate to a content of about 55% and containing 41.1% by weight phenol. It was found by analysis to contain 2761 ppm of tetramethylammonium cation and 0.51% by weight organic bromide (about 79% of total bromide originally present). The total amount of ionic bromide in the mixture was 136 ppm. The extractant was an aqueous hydrogen bromide solution (3.86% by weight hydrogen bromide), with the bromide level increased to 2 equivalents per equivalent of tetramethylammonium cation (TMAC) (0.375 mmol total aqueous bromide) by the addition of aqueous sodium bromide solution (3.99% by weight hydrogen bromide), when necessary.

In each experiment, 5 parts of organic mixture was intimately contacted for 4 minutes with 5 parts of extractant. The organic and aqueous phases were then separated and each phase was analyzed. The results are given in the following table. Distribution coefficient ("Dist. coeff.") is the ratio of the weight of TMAC in the aqueous phase to its weight in the organic phase. In Experiments 4a–4b and 6a–6b, no sodium bromide was employed; on the other hand, no hydrogen bromide was employed in Experiments 8a–9b.

equivalents (relative to palladium) of lead as lead(II) oxide, 2 equivalents of titanium as titanyl acetylacetonate (TiO (acac)$_2$), and 746 equivalents of sodium bromide. Tetraglyme comprises about 6% of the initial weight of the mixture. There is also present 30 grams of molecular seives (type 3A) for absorption of water. At the end of 2.5 hours of reaction there is present about 1.21% by weight bromophenols (approximately 500 equivalents relative to palladium) and 20.2% by weight of diphenyl carbonate. A sample of this reaction mixture is extracted with an equal weight of aqueous hydrobromic acid containing an equal number of moles of HBr as there are moles of bromophenols in the sample of the reaction mixture. The fraction of sodium extracted from the organic phase is X %. A second extraction is performed where the extractant is water only. The fraction of sodium extracted from the organic into the aqueous phase is Y %. The fraction of sodium extracted in the first example (X%) is significantly greater than that in the second example (Y%).

EXAMPLE 11

A reaction mixture is generated from a catalyst package using 15 ppm palladium as palladium acetylacetonate, 55 equivalents of lead as lead(II) oxide (relative to palladium), 2 equivalents of titanium as titanyl acetylacetonate (TiO

| Ex. | Temp., °C. | HBr in extractant, mmol | NaBr in extractant, mmol | Molar ratio, hydrogen ion/TMAC | TMAC, aq. phase, ppm | Ionic Bromide, aq. phase, ppm | Phenol, aq. phase, wt. % | TMAC, org. phase, ppm | Ionic Bromide, org. phase, ppm | Dist. coeff. |
|---|---|---|---|---|---|---|---|---|---|---|
| 3a | 75 | 0.188 | 0.188 | 1 | 2663 | 5461 | 5.96 | 844 | 133 | 3.15 |
| 3b | 75 | 0.188 | 0.188 | 1 | 3122 | 6512 | 5.99 | 727 | 139 | 4.30 |
| 4a | 75 | 0.375 | 0 | 2 | 3091 | 6021 | 6.08 | 573 | 156 | 5.40 |
| 4b | 75 | 0.375 | 0 | 2 | 3191 | 6042 | 6.10 | 527 | 165 | 6.05 |
| 5a | 95 | 0.188 | 0.188 | 1 | 3093 | 6463 | 6.78 | 746 | 104 | 4.15 |
| 5b | 95 | 0.188 | 0.188 | 1 | 2970 | 6283 | 6.66 | 745 | 120 | 3.99 |
| 6a | 95 | 0.375 | 0 | 2 | 3605 | 6894 | 7.08 | 668 | 227 | 5.40 |
| 6b | 95 | 0.375 | 0 | 2 | 3635 | 6831 | 7.24 | 450 | 105 | 8.08 |
| 7a | 85 | 0.282 | 0.094 | 1.5 | 2973 | 6239 | 6.56 | 530 | 98 | 5.61 |
| 7b | 85 | 0.282 | 0.094 | 1.5 | 3059 | 6221 | 6.70 | 689 | 136 | 4.44 |
| 7c | 85 | 0.282 | 0.094 | 1.5 | 3108 | 6282 | 6.64 | 508 | 108 | 6.12 |
| 7d | 85 | 0.282 | 0.094 | 1.5 | 3222 | 6621 | 6.59 | 572 | 133 | 5.63 |
| 8a | 75 | 0 | 0.375 | 0 | 1285 | 5675 | 5.83 | 1102 | 116 | 1.17 |
| 8b | 75 | 0 | 0.375 | 0 | 1364 | 5997 | 5.88 | 1190 | 127 | 1.15 |
| 9a | 95 | 0 | 0.375 | 0 | 1716 | 6179 | 6.87 | 953 | 95 | 1.80 |
| 9b | 95 | 0 | 0.375 | 0 | 1675 | 5895 | 6.88 | 878 | 83 | 1.91 |

It is apparent from the results in the table that the use of aqueous hydrogen bromide, as in Experiments 3a–7d, affords a significant increase in the weight of TMAC in the aqueous phase in comparison with Experiments 8a–9b, where all the bromide was provided as sodium bromide. A comparison of Experiments 4a4b and 6a–6b with Experiments 3a–3b and 5a–5b demonstrates that no benefit is provided by the use of sodium bromide. On the other hand, a comparison of Experiments 8a–8b with 3a–3b, and of Experiments 9a–9b with 5a–5b, shows a significant improvement by the use of hydrogen bromide.

In addition, the density difference between the aqueous and organic phases was within experimental error of 0.08 or above in all experiments except 9b. Thus, the only one not satisfying this preferred criterion was one of the controls.

EXAMPLE 10

A reaction mixture is generated from a catalyst package using 15 ppm palladium as palladium acetylacetonate, 55

(acac)$_2$), and 746 equivalents of sodium bromide, 114 equivalents of sodium hydroxide, and tetraglyme comprising 5% of the initial weight of the mixture. At the end of one hour of reaction, the mixture contains about 1.13% bromophenols (approximately 470 equivalents relative to palladium) and 15.3% of diphenyl carbonate. A sample of this reaction mixture is extracted with an equal weight of aqueous hydrobromic acid containing an equal number of moles of HBr as there are moles of bromophenols and sodium hydroxide initially present in the sample of reaction mixture. The fraction of sodium extracted from the organic phase is X %. A second extraction is performed where the aqueous extractant is water only. The fraction of sodium extracted from the organic into the aqueous phase is Y %. The fraction of sodium extracted in the first example (X %) is significantly greater than that in the second example (Y %).

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

What is claimed is:

1. A method for removal and recycle of ionic bromide-containing catalytic materials from a composition comprising a substantially water-insoluble organic material and a bromide source, which comprises the steps of contacting said composition with an aqueous acidic solution comprising bromide ions, thereby regenerating said bromide source, and extracting said bromide source with an aqueous liquid.

2. A method according to claim 1 wherein the organic material is a diaryl carbonate.

3. A method according to claim 2 wherein the diaryl carbonate is diphenyl carbonate.

4. A method according to claim 2 wherein the bromide-containing catalytic material is an alkali metal bromide, an alkaline earth metal bromide, an onium bromide, a phosphonium bromide, a sulfonium bromide, a tetraalkylammonium bromide, or a hexaalkylguanidinium bromide.

5. A method according to claim 2 wherein the catalytic material also comprises at least one compound of a Group 8, 9, or 10 metal having an atomic number of at least 44.

6. A method according to claim 5 wherein the metal is palladium.

7. A method according to claim 2 wherein the catalytic material also comprises at least one metal compound as an inorganic co-catalyst.

8. A method according to claim 7 wherein the metal compound is of a metal other than cobalt.

9. A method according to claim 8 wherein the metal compound is one of lead, manganese, cerium, titanium, or copper, and mixtures thereof.

10. A method according to claim 9 wherein the metal compound is one of lead.

11. A method according to claim 2 wherein the acidic solution is a hydrogen bromide solution.

12. A method according to claim 2 wherein the aqueous acidic solution contains at least a 10% molar excess of acid with respect to bromide source originally present.

13. A method according to claim 2 wherein the aqueous extraction liquid is the aqueous acidic solution.

14. A method according to claim 2 wherein the aqueous extraction liquid is water.

15. A method according to claim 2 wherein the composition further comprises at least one hydroxyaromatic compound.

16. A method according to claim 15 which further comprises a prior step of removing a major proportion of hydroxyaromatic compound from the organic liquid.

17. A method according to claim 16 wherein the hydroxyaromatic compound is removed by vacuum stripping.

18. A method according to claim 16 wherein about 75–90% by weight of the hydroxyaromatic compound is removed.

19. A method according to claim 2 wherein the aqueous acidic solution and organic material differ in density by at least 0.08 grams per milliliter.

20. A method for removal and recycle of sodium bromide, tetraalkylammonium bromide, or hexaalkylguanidinium bromide from a composition comprising said sodium bromide, tetraalkylammonium bromide, or hexaalkylguanidinium bromide, diphenyl carbonate, and phenol, which comprises contacting said composition with an aqueous hydrogen bromide solution, thereby regenerating said sodium bromide, tetraalkylammonium bromide, or hexaalkylguanidinium bromide, and extracting said bromide source with water.

21. A method according to claim 19 which further comprises a prior step of removing about 75–90% by weight of the phenol from the organic liquid by vacuum stripping.

* * * * *